US011771929B2

(12) United States Patent
Riccio

(10) Patent No.: US 11,771,929 B2
(45) Date of Patent: Oct. 3, 2023

(54) PATIENT RESPIRATORY MASK WITH INTEGRATED MICROPHONE AND METHOD OF PATIENT COMMUNICATION UTILIZING THE SAME

(71) Applicant: Lucca Ventures, Inc., Southington, CT (US)

(72) Inventor: Lucca Riccio, Southington, CT (US)

(73) Assignee: Lucca Ventures, Inc., Southington, CT (US)

( * ) Notice: Subject to any disclaimer, the term of this patent is extended or adjusted under 35 U.S.C. 154(b) by 0 days.

(21) Appl. No.: 17/989,385

(22) Filed: Nov. 17, 2022

(65) Prior Publication Data

US 2023/0080573 A1 Mar. 16, 2023

Related U.S. Application Data

(63) Continuation of application No. 17/089,903, filed on Nov. 5, 2020, which is a continuation of application (Continued)

(51) Int. Cl.

*A62B 18/08* (2006.01)
*A61M 16/06* (2006.01)
(Continued)

(52) U.S. Cl.

CPC ........... *A62B 18/08* (2013.01); *A61M 16/021* (2017.08); *A61M 16/06* (2013.01); (Continued)

(58) Field of Classification Search

CPC ................ A61M 16/021; A61M 16/06; A61M 16/0875; A61M 2205/3375; (Continued)

(56) References Cited

U.S. PATENT DOCUMENTS 2,953,129 A * 9/1960 Bloom .................. A62B 18/08 128/201.19
3,314,424 A * 4/1967 Berman ................. A62B 18/08 128/201.19

(Continued)

FOREIGN PATENT DOCUMENTS

CN 105167252 A 12/2015
EP 1 657 955 A1 5/2006

(Continued)

OTHER PUBLICATIONS

Written Opinion of the International Searching Authority and International Search Report for International Application No. PCT/US2017/038434, dated Aug. 29, 2017 (16 pp).

(Continued)

*Primary Examiner* — Annette Dixon
(74) *Attorney, Agent, or Firm* — Wiggin and Dana LLP

(57) ABSTRACT

The present disclosure presents a patient respiratory mask that is configured to pick up patient speech from within the patient respiratory mask utilizing a microphone and to transmit that speech to a speaker or other communications device and a method of patient communication utilizing the same.

22 Claims, 5 Drawing Sheets

Related U.S. Application Data

No. 15/611,136, filed on Jun. 1, 2017, now Pat. No. 10,857,399.

(60) Provisional application No. 62/353,099, filed on Jun. 22, 2016.

(51) Int. Cl.

| | |
|---|---|
| ***A61M 16/00*** | (2006.01) |
| ***A61M 16/08*** | (2006.01) |
| ***G10L 15/22*** | (2006.01) |
| ***H04R 1/02*** | (2006.01) |
| *H04R 1/08* | (2006.01) |

(52) U.S. Cl.

CPC ......... *A61M 16/0875* (2013.01); *G10L 15/22* (2013.01); *H04R 1/028* (2013.01); *A61M 2205/3375* (2013.01); *A61M 2205/3592* (2013.01); *A61M 2205/8206* (2013.01); *G10L 2015/223* (2013.01); *H04R 1/083* (2013.01); *H04R 2410/03* (2013.01); *H04R 2420/07* (2013.01)

(58) Field of Classification Search

CPC .. A61M 2205/3592; A61M 2205/8206; A62B 18/08; A62B 9/04; G10L 15/22; G10L 2015/223; H04B 10/00; H04R 1/028; H04R 1/083; H04R 2410/03; H04R 2420/07; Y10T 29/49002

See application file for complete search history.

(56) References Cited

U.S. PATENT DOCUMENTS

| | | | | |
|---|---|---|---|---|
| 4,072,831 | A * | 2/1978 | Joscelyn | H04R 1/083 381/385 |
| 4,901,356 | A * | 2/1990 | Bauer | H04R 1/083 381/385 |
| 5,060,308 | A * | 10/1991 | Bieback | A62B 18/08 398/115 |
| 5,138,666 | A * | 8/1992 | Bauer | A62B 18/08 381/385 |
| 6,121,881 | A | 9/2000 | Bieback et al. | |
| 6,134,331 | A * | 10/2000 | Bækgaard | A61B 7/04 381/67 |
| 6,619,288 | B2 | 9/2003 | Demers et al. | |
| 7,269,266 | B2 | 9/2007 | Anjanappa et al. | |
| 7,342,502 | B2 | 3/2008 | Harkins et al. | |
| 7,532,934 | B2 | 5/2009 | Lee et al. | |
| 8,487,771 | B2 | 7/2013 | Hsieh et al. | |
| 8,616,205 | B2 | 12/2013 | Tobias et al. | |
| 8,818,522 | B2 | 8/2014 | Mass et al. | |
| 8,844,521 | B2 | 9/2014 | McCarthy | |
| 9,227,032 | B2 | 1/2016 | Kwok et al. | |
| 9,227,034 | B2 | 1/2016 | Kapust et al. | |
| 9,364,625 | B2 | 6/2016 | Silver et al. | |
| 9,498,658 | B2 | 11/2016 | Kihlbertg | |
| 9,642,557 | B2 | 5/2017 | Gavish et al. | |
| 10,136,225 | B2 | 11/2018 | Register et al. | |
| D877,886 | S | 3/2020 | Register et al. | |
| 10,681,469 | B2 | 6/2020 | Register et al. | |
| 10,857,399 | B2 * | 12/2020 | Riccio | A61M 16/021 |
| 2005/0096096 | A1 | 5/2005 | Birli et al. | |
| 2005/0197172 | A1 | 9/2005 | Davies | |
| 2005/0213782 | A1 | 9/2005 | Miller et al. | |
| 2008/0216835 | A1 | 9/2008 | McGinnis et al. | |
| 2009/0205662 | A1 | 8/2009 | Kwok et al. | |
| 2013/0324788 | A1 | 12/2013 | Holley et al. | |
| 2015/0020815 | A1 | 1/2015 | Gabriel et al. | |
| 2015/0101600 | A1 | 4/2015 | Miller | |
| 2015/0206408 | A1 | 7/2015 | Lalonde et al. | |
| 2015/0217143 | A1 * | 8/2015 | Palmer | A62B 9/04 29/592.1 |
| 2016/0001110 | A1 | 1/2016 | Hamilton | |
| 2016/0095997 | A1 | 4/2016 | Kapust et al. | |
| 2016/0101301 | A1 | 4/2016 | Kihlberg | |
| 2016/0199602 | A1 | 7/2016 | Fernandez | |
| 2021/0052923 | A1 * | 2/2021 | Riccio | A61M 16/021 |

FOREIGN PATENT DOCUMENTS

| | | | |
|---|---|---|---|
| EP | 2673032 | A1 | 12/2013 |
| EP | 2776101 | A1 | 9/2014 |
| GB | 2 371 493 | A | 7/2002 |
| WO | 2000/069337 | A1 | 11/2000 |
| WO | 2012/106774 | A1 | 8/2012 |
| WO | 2013/067580 | A1 | 5/2013 |
| WO | 2013/071458 | A1 | 5/2013 |

OTHER PUBLICATIONS

Supplementary European Search Report, European Patent Application No. 17 81 6101, dated Jan. 14, 2020 (2 pp).

Cairns, Rebecca. A Japanese Robotics Startup has invented a smart mask that translates into eight languages. CNN Business [online]. Nov. 13, 2020 [retrieved on Oct. 29, 2021]. Retrieved from the internet: <URL:cnn.com/2020/08/03/japanese-robotics-smart-face-mask-spc-intl/index.html>.

* cited by examiner

PATIENT RESPIRATORY MASK WITH INTEGRATED MICROPHONE AND METHOD OF PATIENT COMMUNICATION UTILIZING THE SAME

CROSS-REFERENCE TO RELATED APPLICATIONS

This patent application is a continuation of U.S. application Ser. No. 17/089,903, filed Nov. 5, 2020, which is a continuation of U.S. application Ser. No. 15/611,136, filed Jun. 1, 2017, which claims priority to U.S. Provisional No. 62/353,099 filed Jun. 22, 2016, each of which are incorporated herein by reference in their entirety.

BACKGROUND

The present disclosure relates patient respiratory masks, and in particular, patient respiratory masks, such as continuous positive air pressure (CPAP) or other (e.g., bi-level positive airway pressure (BiPAP)) devices, said respiratory masks that include a microphone, the microphone configured to interface with a wired or wireless speaker and/or a wired or wireless communications device, such as a telephone.

In a clinical setting, with a patient that requires the use of a respiratory mask that restricts the ability to communicate naturally, coherent conversation with visitors or via telephone is universally difficult. This is due, at least in part, to the intervening plastic material as well as to noise of the airflow and machinery.

Accordingly, there is a need in the art for a patient respiratory mask that is configured to pick up patient speech from within the patient respiratory mask or associated accessories, utilizing a microphone, and transmitting that speech to an external speaker or other communications device.

SUMMARY

The above-described and other problems and disadvantages of the prior art are overcome or alleviated by the present patient respiratory mask that includes a microphone, the microphone configured to interface with a wired or wireless speaker and/or a wired or wireless communications device, such as a telephone.

In exemplary embodiments, the microphone is a noise-cancelling microphone. In further embodiments, the microphone includes or is associated with at least one noise filter. In further exemplary embodiments, one or more of the microphone, speaker and communications device is in a wireless configuration.

In further exemplary embodiments, an on-board speaker is integrated into a portion of the respiratory mask coupler. In further exemplary embodiments, a speaker is external to the mask coupler.

In additional exemplary embodiments, the patient respiratory mask includes an internal and/or coupler adapted noise cancelling microphone with a short-range wireless (radio frequency) technology standard, e.g., Bluetooth®, capability. In further exemplary embodiments, the microphone signal is processed utilizing noise-cancelling sound processing. In exemplary embodiments, the microphone is attached to or built into a respiratory mask or mask fluid delivery tube.

In additional exemplary embodiments, the respiratory mask includes a coupler between a fluid delivery tube and a facial mask portion, the coupler including one or more of a microphone, speaker, wiring, processor, or communications device. In exemplary embodiments, one or more of the preceding elements are embedded in or provided through a portion of the coupler. In further exemplary embodiments, one or more of the elements described herein are embedded in or provided through a device connected to the coupler via power and/or signal wiring.

In further exemplary embodiments, the microphone is configured to wirelessly transmit a patient's voice, via Bluetooth® technology, to a Bluetooth® speaker in proximity to and in communication with the Bluetooth® transmitter. In further exemplary embodiments, the microphone is configured to wirelessly transmit a patient's voice, via Bluetooth® technology, to a Bluetooth®-enabled smartphone in proximity to and in communication with the Bluetooth® speaker and/or the Bluetooth® transmitter. While a Bluetooth® speaker and an exemplary Bluetooth® smartphone are specifically described, the present disclosure contemplates other Bluetooth® communications devices. And while Bluetooth® is specifically described, the present disclosure contemplates other wireless technologies, including but not limited to Wi-Fi.

The above-discussed and other features and advantages of the present invention will be appreciated and understood by those skilled in the art from the following detailed description and drawings.

BRIEF DESCRIPTION OF THE DRAWINGS

Referring now to the drawings, wherein like elements are numbered alike in the following FIGURES.

DETAILED DESCRIPTION

As was noted above, the present disclosure relates to a patient respiratory mask that includes a microphone disposed thereon, the microphone is configured to interface with a wired or wireless speaker and/or a wired or wireless communications device, such as a telephone. While the following is described in reference to various exemplary embodiments, the present disclosure is not so limited.

In some exemplary embodiments, the microphone is a noise-cancelling microphone. In further embodiments, the microphone includes or is associated with at least one noise filter. In further exemplary embodiments, one or more of the microphone, speaker and communications device is wireless. It is to be understood that reference to a component, such as a microphone, speaker, etc., as being wireless or transmitting wirelessly encompasses configurations wherein such device is connected to a component that includes a wireless transmitter and/or receiver. Accordingly, any reference herein to a "wireless" component should be read to encompass such a construction.

In further exemplary embodiments, an on-board speaker is integrated into a portion of the respiratory mask. In further exemplary embodiments, a speaker is external to the mask.

As we have noted, in exemplary embodiments, the patient respiratory mask includes an internal and/or coupler- or tube-adapted noise-cancelling microphone with wireless, e.g., Bluetooth®, capability. In exemplary embodiments, the microphone is attached to or built into a respiratory mask, a coupler designed to attach to the mask tube interface, or mask fluid delivery tube (e.g., for oxygen, air or some other gas). In additional exemplary embodiments, the coupler includes one or more of a microphone, a speaker, wiring, processor and a communications device. In exemplary embodiments one or more of the preceding elements are embedded in or provided through a portion of the coupler.

As we have also noted, further exemplary embodiments, the microphone wirelessly transmits a patient's voice, via Bluetooth® technology, to a Bluetooth® speaker in proximity to and in communication with the Bluetooth® transmitter. Reference herein to a "Bluetooth®" device refers to a device that is enabled to use Bluetooth® technology.

In further exemplary embodiments, the microphone wirelessly transmits a patient's voice, via Bluetooth® technology, to a Bluetooth® smartphone in proximity to and in communication with the Bluetooth® speaker and/or Bluetooth® transmitter. While a Bluetooth® speaker and an exemplary Bluetooth® smartphone are specifically described, the present disclosure contemplates other Bluetooth® communications devices.

Figure 1:
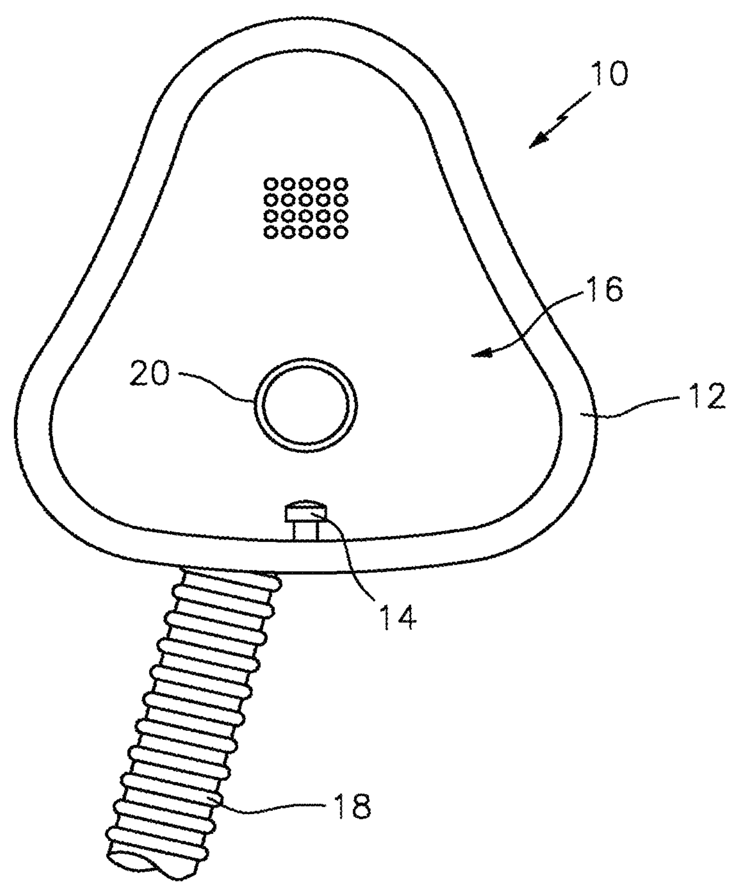
FIG. 1 is a rear elevation view of an exemplary respiratory mask including a microphone in accordance with exemplary embodiments of the present disclosure.

Referring now to FIG. 1, one exemplary patient respiratory mask in accordance with the present disclosure includes an exemplary microphone provided therein. In exemplary embodiments, the respiratory mask is a CPAP (or BIPAP) respiratory mask, shown generally at 10, with a mask portion 12 and a microphone 14 that is incorporated within a fluid airspace, shown generally at 16, of the mask 10 near the mouth (not shown) of a patient. The exemplary mask also includes a fluid delivery tube 18 and at least one mask inlet 20.

In exemplary embodiments, the microphone 14 is mounted on or is provided within the material of the mask. In another exemplary embodiment, the microphone is provided in a separate microphone tube (not shown) that may extend at least partially into the fluid airspace of the mask 10. In further exemplary embodiments, the microphone tube is at least partially sealed, for example via plastic or a membrane that is at least moderately transparent to sound but that also separately maintains the integrity of the fluid airspace 16 within the respiratory mask 10. Such an exemplary microphone tube may be provided within or be mounted to the respiratory mask 10, a fluid delivery tube 18, or any coupler 22 or portions intermediate the fluid delivery tube 18 the respiratory mask 10.

Figure 2:
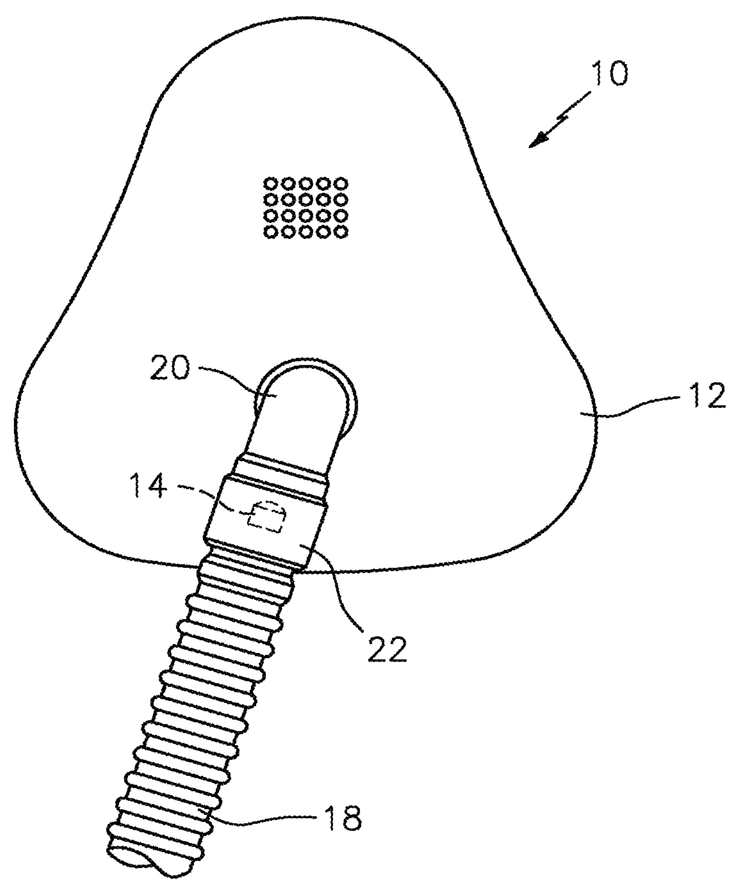
FIG. 2 is a perspective view of an exemplary respiratory mask utilizing a microphone coupler provided on the fluid delivery tube near the respiratory mask in accordance with exemplary embodiments of the present disclosure.
Figure 3:
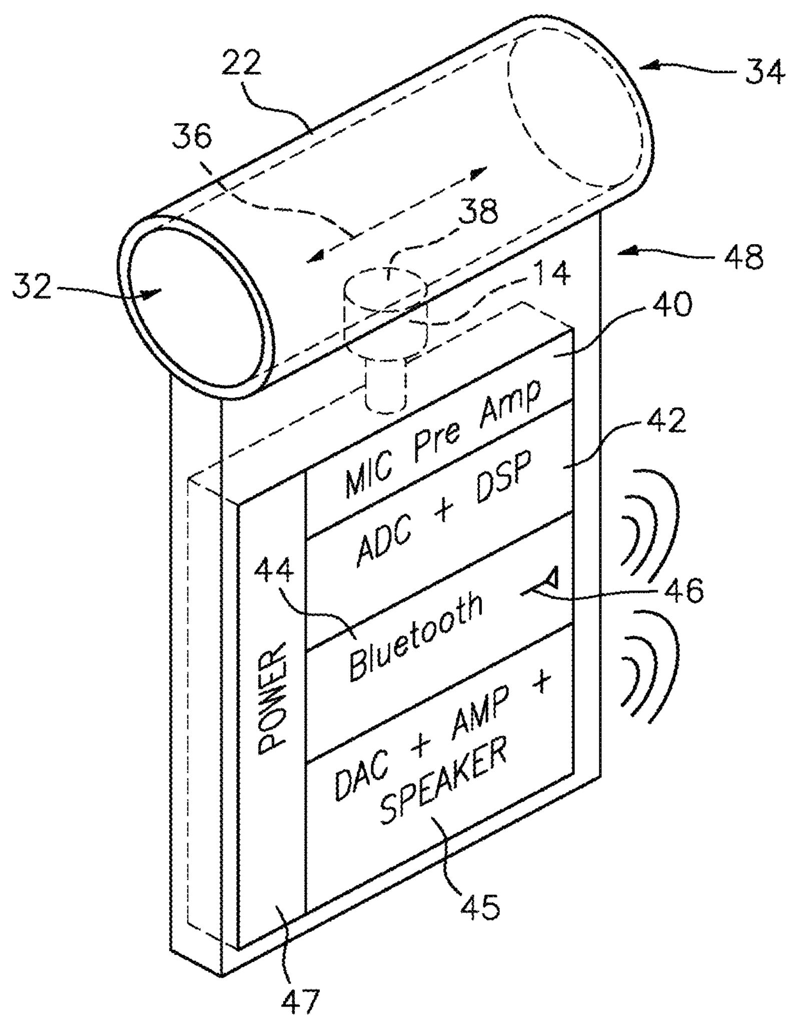
FIG. 3 is a perspective view of an exemplary coupler device incorporating a microphone, including a schematic of communications components for the coupler in accordance with exemplary embodiments of the present disclosure.

Referring now to FIG. 2, another exemplary patient respiratory mask 10 incorporates such Bluetooth® microphone 14 into a coupler 22 that is positioned between the fluid delivery tube 18 and the respiratory mask 10. In exemplary embodiments, the coupler 22 is sized and configured to provide a friction fit for the mask inlet 20 on one side and for the fluid delivery tube 18 on the other side. Referring to FIG. 3, an exemplary coupler 22 includes a mask inlet side, shown generally at 32, a fluid supply tube side, shown generally at 34, with bulk air flow traversing the interior of the tube generally at the arrows of 36.

In an exemplary embodiment, a microphone 14 is separated from the bulk air flow 36 by a filter 38, which may be configured to filter one or more sound characteristics or to simply shield the microphone from bulk air flow. The filter 38 may be a membrane, acoustic mesh, or any other convenient sound transmitting material.

In the illustrated exemplary embodiment, the microphone is illustrated as being operatively connected to a microphone pre-amplifier 40, an equalization component 42 (for example an analog to digital converter (ADC) and digital signal processor (DSP)), a Bluetooth® transmitter 44, a sound output component, such as a digital to analog converter (DAC), amplifier (Amp) and speaker 45, an antenna 46 and a power supply 47, such as a battery or wired power adapter. These components are illustrated in this exemplary embodiment as being both connected to the microphone and as being housed on a protruding portion 48 of the coupler 22. However, it should be recognized that the microphone may be configured on-board the coupler 22 with more or fewer associated components, with some components or processes omitted or performed elsewhere, e.g., on the exterior of the coupler 22, remote from the coupler 22, etc.

In exemplary embodiments, the coupler may be configured to attach to the fluid delivery tube, regardless of any variation in tube diameter (e.g., differences in configurations warranting use of a 19 mm standard tube vs. a 15 mm thin tube). Thus, exemplary embodiments provide a universal attachment (e.g., as a clip on, etc., as shown in FIG. 4) configured to fit a wide array of tubes and breathing apparatuses.

Figure 4A:
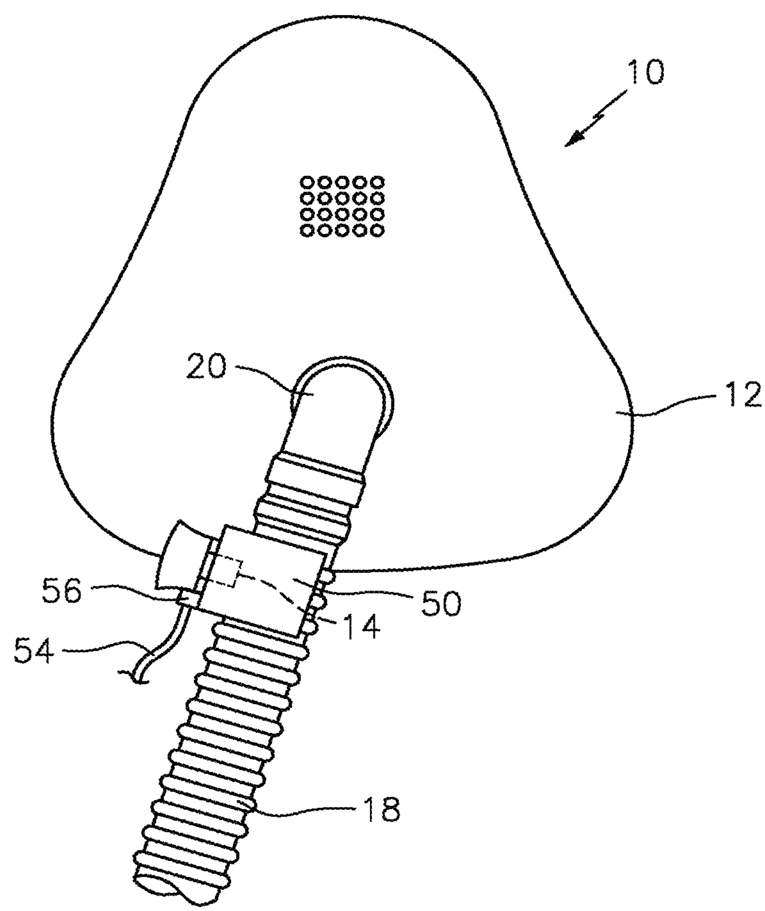
FIG. 4A is a perspective view of an exemplary clip-on accessory including a microphone in accordance with the exemplary embodiments of the present disclosure.
Figure 4B:
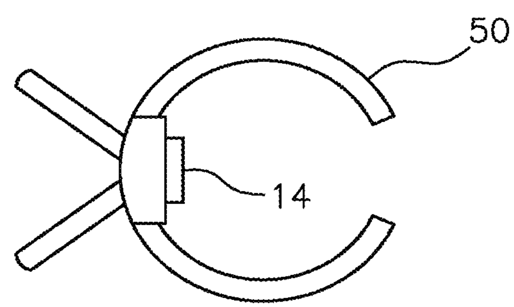
FIG. 4B is a side elevation view of an exemplary clip-on accessory including a microphone in accordance with the exemplary embodiments of the present disclosure.

In other exemplary embodiments, the microphone or other electronic components are configured to attach externally (for example as a clip-type attachment, among others) to the respiratory mask 10 but in close proximity to the patient's fluid airspace (see 16 in FIG. 1). Referring now to FIG. 4A, a clip 50 is illustrated with a microphone 14 provided on an underside of the clip. In exemplary embodiments, the clip 50 also interfaces with a power and signal wire 54 via a port 56. While such a clip may be configured to attach anywhere that is convenient to place the microphone 14 near a sound transmitting surface, for example the mask inlet 20 of mask 10 or an exterior portion of a coupler 22, FIG. 4 illustrates provision of the clip 50 over a portion of the fluid delivery tube 18, with the microphone against or proximate the material of the fluid delivery tube to pick up sound vibrations transmitted through the fluid delivery tube. It should be recognized that while FIG. 4 illustrates a wired configuration, the microphone can also be configured with a battery and a wireless (e.g., Bluetooth®) transmitter. FIG. 4B illustrates an exemplary side elevation view of the clip 50, with microphone 14 positioned to be near fluid delivery tube 18 in an installed position.

Figure 5:
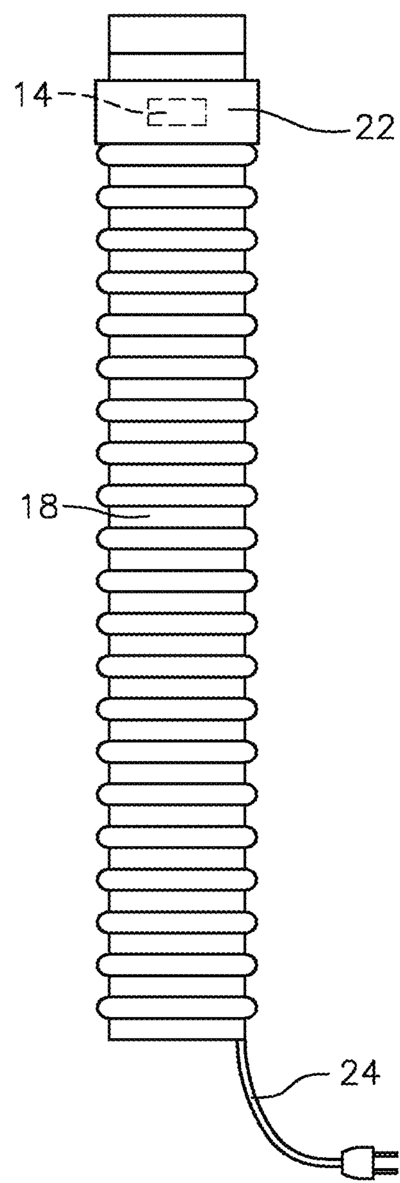
FIG. 5 is a front elevation view of an exemplary wired tube and respiratory mask coupler including a microphone in accordance with exemplary embodiments of the present disclosure.

Referring now to FIG. 5, an exemplary fluid delivery tube 18 is illustrated as including an integrated coupler 22 that incorporates an exemplary microphone 14 (see FIG. 2) therein and is attachable to or integral to respiratory fluid delivery tube 18. An exemplary power cord 24 runs at least along a portion of the fluid delivery tube 18 to the microphone 14 (which may be configured in a wired or wireless, e.g., Bluetooth®, arrangement). As we have noted above, the coupler may also include other components, such as processing or filtering components, a wireless transmitter, etc., in addition to or alternative to the microphone, such as a speaker, wiring or any other type of communications device.

In further exemplary embodiments, the microphone 14 may be configured as a wired microphone utilizing the exemplary cord 24 or another cord for data transmission. In additional exemplary embodiments, the microphone may be wireless and may be connected to a battery source, with no cords running along a portion of the fluid delivery tube 18.

Figure 6:
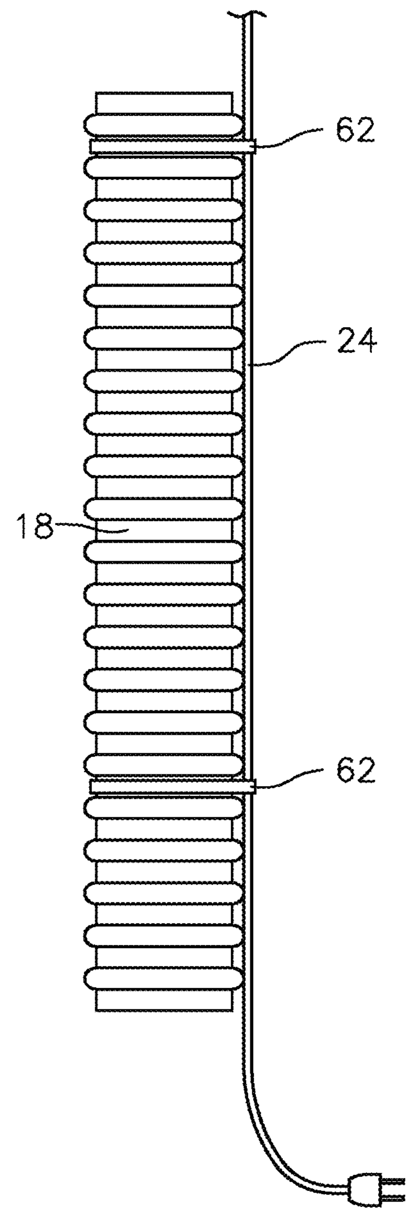
FIG. 6 is a side elevation view of exemplary tube and cord lengths secured to one another via multiple harness clips in accordance with exemplary embodiments of the present disclosure.

In further exemplary embodiments, an exemplary cord can be configured with one or more clips to secure it to the fluid delivery tube 18 or as an integral part of the fluid delivery tube 18, for example embedded or permanently attached to the fluid delivery tube 18 or to a fluid delivery tube wiring harness. Exemplary wire harness clips 62 are illustrated as attaching a cord 24 to fluid delivery tube 18 in FIG. 6. In exemplary embodiments, the cord 24 is configured as a wiring harness secured at one or more places via harness clips 62, with the cord connectable to a coupler 22 (as in FIGS. 2 and 3) or a mask (as in FIG. 1).

For any wired configurations, the remote (from the mask) end of the cord 24 may be configured to connect to additional components, such as a speaker, processor, network, power, etc.

Exemplary embodiments contemplate non-rechargeable, battery-driven Bluetooth® microphones as well as rechargeable battery Bluetooth® microphones with a port or cable or wireless connection for recharging via an external power source, or directly corded microphones (providing constant power).

In exemplary embodiments, the patient respiratory mask, inclusive of the Bluetooth® microphone, is configured as a disposable device. In exemplary embodiments, one or more components, such as the mask, coupler or hose, is configured as a disposable product to have a pre-determined working lifetime. In further exemplary embodiments, life indicators may be used to identify an end of the working respirator mask lifetime determined from unpacking from a sterile field. In a further exemplary embodiment, a battery in communication with the microphone is configured to expire or switch off at end of the working respirator mask lifetime.

In other exemplary embodiments, the patient respiratory mask and/or fluid delivery tube is configured to be reusable, with the Bluetooth® microphone being at least partially water resistant. In further exemplary embodiments, the Bluetooth® microphone is waterproof or is housed in a waterproof enclosure. In such exemplary embodiments, the patient respiratory mask and/or tube may be configured with a Bluetooth® microphone configured to withstand cleaning via use of cleaning agents, e.g., enzymatic cleaning solutions, rinses, disinfectants and pasteurizations, among others. Further exemplary embodiments provide a Bluetooth® microphone or microphone enclosure configured to withstand the effects of cleaning as well as effects of drying at utility or other stations.

Exemplary embodiments of the present disclosure also relate to an exemplary system with a patient respiratory mask positioned on a patient, the respiratory mask including a Bluetooth® noise cancelling microphone within or adjacent to the patient's fluid airspace, and at least one external Bluetooth® communications device. In the illustrated exemplary embodiment, a Bluetooth® speaker and a Bluetooth® smartphone are illustrated as being in communication with the microphone. In exemplary embodiments, at least the microphone and one external Bluetooth® communication device are pre-paired to permit instantaneous connection when within the proper proximity. In other exemplary embodiments, the Bluetooth® microphone continually broadcasts pairing information and is open for pairing subject to confirmation by the external Bluetooth® communications device. Other exemplary communications devices are also contemplated herein, including, without limitation, personal assistants, including media platforms such as the Google Home or Amazon Echo/Tap/Alexa, etc., that also might have a speaker that is usable for patient communications as well as the ability to accept commands for any of its functions (e.g., to play music or call someone via voice over Internet protocol or other means). Other exemplary embodiments have a speaker integral with the mask, coupler or fluid tube. Additionally, other communications protocols may be used in conjunction with the above-described wireless protocols and others (e.g., non-Bluetooth® wireless protocols), such as Wi-Fi.

As we have noted, a speaker or other communications device may be external or may be integrated into the mask portion, coupler or fluid delivery tube. Additionally, such speaker or other communications device can be configured to communicate wirelessly or in a wired mode. In a further exemplary aspect, both modes are configured, and the system is configured to automatically or manually (via a switch or application) switch modes.

In further exemplary embodiments an application running on a processor controls one or more aspects of the system, including without limitation: speaker or communications device mode; noise filtering/canceling or processing parameters; microphone parameters; wireless connections to devices; and monitoring for new devices in range.

In further exemplary embodiments, power for one or more components is supplied by a power cable with any convenient terminal ends, for example 110 volt outlet termination, USB, lightning connector, etc.

In other exemplary embodiments, bone induction or an in-ear, behind the ear or in-canal hearing aid provides or delivers a sound signal to the patient, with bone induction or hearing aid equipment wired to or wirelessly communicating with the respiratory mask system.

In exemplary embodiments, when the user (patient) of the respiratory mask speaks, their voice will be captured by the noise canceling microphone as the sound hits the interior structure of the mask and/or travels down the tube. Once the voice is captured in the device, it is transferred via Bluetooth® technology to a free-standing speaker where their voice will be amplified. In other exemplary embodiments, the voice is transferred to a speaker on the mask, coupler or tube where the voice will be amplified.

In other exemplary embodiments, the system is configured to distinguish between direct human interaction (conversation) and digital interaction (e.g., voice signals from a mobile phone) and automatically switch output to one of plural possible wireless communications devices depending on the detected signal. Alternative automatic or manual switching is further contemplated herein with regard to exemplary embodiments, for switching between a nearby Bluetooth® speaker and a communications device (e.g., a mobile telephone, facilitating patient conversation with a remote individual). In other embodiments, multiple Bluetooth® devices may be connected at the same time via bridging capabilities. Such a switching or bridging capability may be e.g., provided alongside the microphone or anywhere in range of the Bluetooth® microphone. In other embodiments, multiple Bluetooth® devices may be connected at the same time via multiple connections or modes.

It will be apparent to those skilled in the art that, while exemplary embodiments have been shown and described, various modifications and variations can be made to the invention disclosed herein without departing from the spirit or scope of the invention. Also, the exemplary implementations described above should be read in a non-limiting fashion, both with regard to construction and methodology. Accordingly, it is to be understood that the various embodiments have been described by way of illustration and not limitation.

What is claimed is:

1. A patient respiratory mask, comprising:

- a mask portion defining an interior airspace, the mask portion comprising an inlet to the interior airspace;
- a fluid delivery tube in fluid communication with the interior airspace to provide positive air pressure from a positive air pressure device when connected with the fluid delivery tube;
- a coupler between the inlet of the mask portion and the fluid delivery tube, the fluid delivery tube connecting with a portion of the coupler substantially below the inlet to the interior airspace of the mask portion; and
- a housing protruding at least partially from the coupler, the housing including a microphone and a speaker arranged at opposing portions of the housing, with the speaker being arranged in a portion of the housing protruding from the coupler, the housing including a microphone tube extending at least partially into the interior airspace of the mask portion to position the microphone within the interior airspace, to pick up speech from the patient;
- the microphone being operatively connected to the speaker by one or more of:
  - an equalization component including an analog to digital converter and a digital signal processor; and
  - a sound output component including a digital to analog converter,
- to amplify the speech of the patient over the speaker.

2. The patient respiratory mask of claim 1, further comprising a processor controlling one or more of microphone parameters, noise filtering, noise cancelling, and noise processing.

3. The patient respiratory mask of claim 2, wherein the processor is connected with the housing by a cord securable to the fluid delivery tube, wherein a first end of the cord is connected with the housing and a second end of the cord is connected with the processor at a location remote from the mask portion.

4. The patient respiratory mask of claim 1, wherein the microphone is operatively connected to the speaker by a wired connection.

5. The patient respiratory mask of claim 4, wherein the microphone and the operatively connected speaker are supplied with power by a battery or power cable.

6. The patient respiratory mask of claim 1, wherein the microphone is operatively connected to the speaker by a wireless connection.

7. The patient respiratory mask of claim 1, wherein the microphone comprises a filter configured to shield the microphone from bulk air flow or to filter one or more sound characteristics.

8. The patient respiratory mask of claim 1, wherein the positive air pressure device is a continuous positive air pressure (CPAP) or bi-level positive air pressure (BiPAP) device.

9. A patient respiratory mask, comprising:

- a mask portion defining an interior airspace, the mask portion comprising an inlet to the interior airspace;
- a fluid delivery tube in fluid communication with the interior airspace to provide positive air pressure from a positive air pressure device when connected with the fluid delivery tube;
- a coupler between the inlet of the mask portion and the fluid delivery tube, the fluid delivery tube connecting with a portion of the coupler substantially below the inlet to the interior airspace of the mask portion;
- a microphone provided through a portion of the coupler, wherein the microphone is positioned within the interior airspace when provided through the coupler to pick up speech from the patient; and
- a speaker operatively connected with the microphone to amplify the speech of the patient;
- wherein the microphone and speaker are arranged in a housing provided through a portion of the coupler, wherein the microphone and speaker are arranged at opposing-portions of the respective housing, with the speaker arranged in a portion of the housing protruding at least partially from the coupler, and wherein the microphone is operatively connected to one or more of:

- an equalization component including an analog to digital converter and a digital signal processor; and
- a sound output component including a digital to analog converter, to amplify the speech of the patient over the speaker.

10. The patient respiratory mask of claim 9, wherein the microphone and speaker are operatively connected by a wired connection.

11. The patient respiratory mask of claim 9, wherein the housing comprises a filter configured to shield the microphone from bulk air flow or to filter one or more sound characteristics.

12. The patient respiratory mask of claim 9, further comprising a processor controlling one or more aspects of the patient respiratory mask including one or more of: speaker or communications device mode, noise filtering/canceling or processing parameters, microphone parameters, wireless connections to external devices, and monitoring for new external devices in range.

13. The patient respiratory mask of claim 9, further comprising a processor controlling one or more of microphone parameters, noise filtering, noise cancelling, and noise processing.

14. The patient respiratory mask of claim 13, wherein the processor is connected with the housing by a cord securable to the fluid delivery tube, wherein a first end of the cord is connected with the housing and a second end of the cord is connected with the processor at a location remote from the mask portion.

15. The patient respiratory mask of claim 9, wherein the positive air pressure device is a continuous positive air pressure (CPAP) or bi-level positive air pressure (BiPAP) device.

16. A communications system, comprising:

- a respiratory mask for wearing by a patient, the respiratory mask comprising:
  - a mask portion defining an interior airspace, the mask portion comprising an inlet to the interior airspace;
  - a fluid delivery tube coupled with the inlet by a coupler, the fluid delivery tube connecting with a portion of the coupler substantially below the inlet to the interior airspace of the mask portion, whereby the fluid delivery tube is in fluid communication with the interior airspace to provide positive air pressure from a positive air pressure device connected with the fluid delivery tube;

a housing, the housing comprising:

a microphone, and a speaker operatively connected with the microphone by a wired connection, the housing enclosing the microphone and speaker, the microphone and speaker arranged at opposing portions of the housing, wherein the microphone is provided within a tubular portion of the housing extending at least partially into the interior airspace of the mask portion to position the microphone in close proximity to the patient's mouth, and wherein the tubular portion of the housing is provided through a portion of the coupler; and a processor controlling one or more aspects of the system, wherein the processor is connected with the housing by a cord securable to the fluid delivery tube, wherein a first end of the cord is connected with the housing and a second end of the cord is connected with the processor remote from the mask portion.

17. The system of claim 16, wherein the speaker and microphone are operatively connected by one or more of:

an equalization component including an analog to digital converter and a digital signal processor; and a sound output component including a digital to analog converter, to amplify the speech of the patient over the speaker.

18. The system of claim 16, wherein the housing comprises a filter configured to shield the microphone from bulk air flow or to filter one or more sound characteristics.

19. The system of claim 16, wherein the tubular portion of the housing is at least partially sealed by a plastic or a membrane at least moderately transparent to sound, and wherein the plastic or membrane maintains the integrity of the interior airspace of the respiratory mask.

20. The system of claim 16, wherein the one or more aspects of the system controlled by the processor include one or more of: speaker or communications device mode, noise filtering/canceling or processing parameters, microphone parameters, wireless connections to external devices, and monitoring for new external devices in range.

21. The system of claim 16, wherein the one or more aspects of the system controlled by the processor include one or more of: microphone parameters, noise filtering, noise cancelling, and noise processing.

22. The system of claim 16, wherein the positive air pressure device is a continuous positive air pressure (CPAP) or bi-level positive air pressure (BiPAP) device.

* * * * *